United States Patent
Frid

(10) Patent No.: US 6,273,084 B1
(45) Date of Patent: Aug. 14, 2001

(54) INHALATION DEVICE

(75) Inventor: Per Frid, Lund (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/214,287

(22) PCT Filed: Oct. 27, 1998

(86) PCT No.: PCT/SE98/01944

§ 371 Date: Dec. 31, 1998

§ 102(e) Date: Dec. 31, 1998

(87) PCT Pub. No.: WO99/25405

PCT Pub. Date: May 27, 1999

(30) Foreign Application Priority Data

Nov. 14, 1997 (SE) .................................................. 9704184

(51) Int. Cl.[7] .................................................. A61M 11/00
(52) U.S. Cl. .................................. 128/200.23; 128/200.14
(58) Field of Search ........................ 128/200.14, 200.18, 128/200.23 OR, 200.24, 203.23

(56) References Cited

U.S. PATENT DOCUMENTS

| 3,429,310 | * | 2/1969 | Jaffe et al. | 128/200.23 |
| 3,636,949 | * | 1/1972 | Kropp | 128/200.23 |
| 3,865,279 | | 2/1975 | James | 222/182 |

FOREIGN PATENT DOCUMENTS

| 0 075 548 A2 | 3/1983 | (EP) . |
| 0 341 967 A2 | 11/1989 | (EP) . |
| 2 164 392 | 3/1986 | (GB) . |

* cited by examiner

Primary Examiner—Glenn K. Dawson
(74) Attorney, Agent, or Firm—Fish & Richardson P.C.

(57) ABSTRACT

An actuator for an inhaler for administering medicament by inhalation, comprising: a main body (1) defining a chamber (4) for receiving a canister (3) containing medicament, and including an outlet (11) through which medicament is in use delivered, the canister (3) being in use acted upon by the user in the delivery of medicament; a cover member (2) rotatable in relation to the main body (1) between a first, closed position in which the outlet (11) is covered and a second, open position in which the outlet (11) is exposed, the cover member (2) including a grip portion (33) which in use is acted upon by the user in the delivery of medicament and includes a surface (33a) having a component facing in the sense of rotation of the cover member (2) from the open to the closed position; characterized in that the main body (1) includes a projecting member (16) which includes a surface (16a) having a component facing in the sense of rotation of the cover member (2) from the closed to the open position behind which the surface (33a) of the grip portion (33) of the cover member (2) is at least partly located in the open position of the cover member (2), whereby in use in the delivery of medicament the surface (33a) of the grip portion (33) of the cover member (2) is caused to be urged behind the surface (16a) of the projecting member (16) of the main body (1) so as to lock the cover member (2) relative to the main body (1).

10 Claims, 4 Drawing Sheets

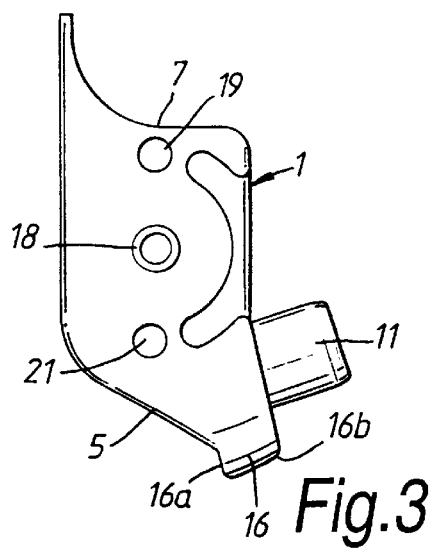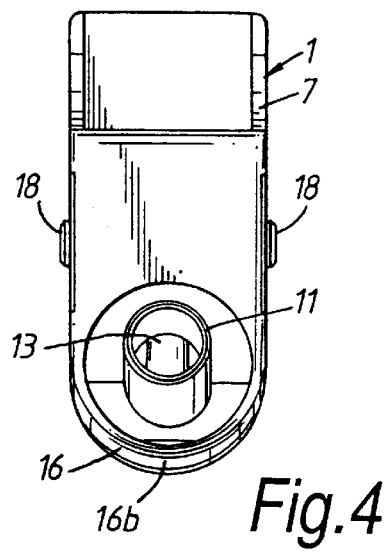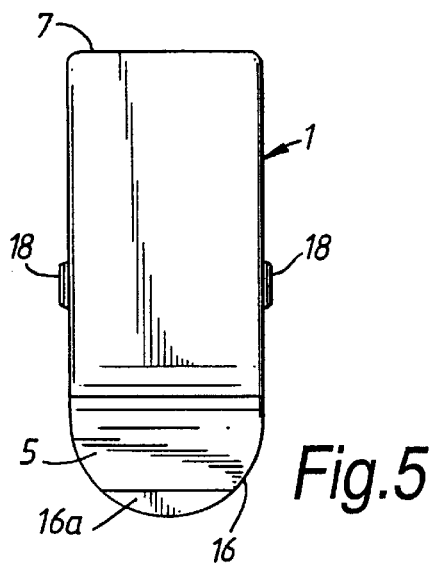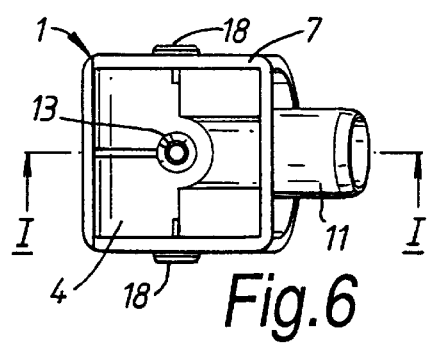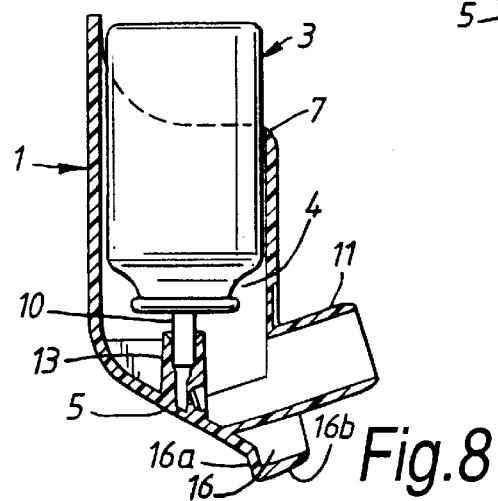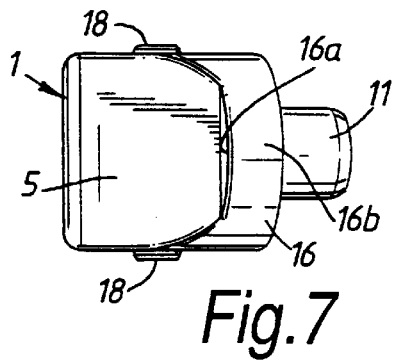

INHALATION DEVICE

The present invention relates to an actuator for an inhaler for administering, in particular nasally, an aerosol based medicament by inhalation and to an inhaler including the same.

One such actuator is disclosed in the applicant's earlier EP-A-0075548. That document discloses an actuator comprising a main body which defines a chamber for receiving an aerosol canister containing medicament and includes an outlet through which medicament is in use delivered for administration. This actuator further comprises a cover member which is rotatable between a closed position in which the cover member covers the outlet and an open position in which the outlet is exposed for use. In the open position the cover member is configured to be acted upon by the thumb of the user, with the force to actuate the canister being applied between the thumb located on the underside of the cover member and typically the index finger located on the exposed base of the canister.

Ordinarily, this actuator has been found to operate satisfactorily. However, users have found that in use in the delivery of medicament the cover member can be unstable and tend to return to the closed position. This instability arises when the user places his/her thumb incorrectly, that is, not in accordance with the user instructions, on the underside of the cover member, which leads to the creation of a turning moment that tends to close the cover member. It will, of course, be appreciated that unwanted closure of the cover member is highly undesirable, particularly when actually applying a force to the same, since a part of the anatomy of the user, the nose in the case of nasal administration, will be trapped between the main body and the cover member.

It is an aim of the present invention to provide an improved actuator for an inhaler for the administration of an aerosol based medicament which overcomes the above-mentioned problem associated with the prior art actuator.

Accordingly, the present invention provides an actuator for an inhaler for administering medicament by inhalation, comprising: a main body defining a chamber for receiving a canister containing medicament, and including an outlet through which medicament is in use delivered, the canister being in use acted upon by the user in the delivery of medicament; a cover member rotatable in relation to the main body between a first, closed position in which the outlet is covered and a second, open position in which the outlet is exposed, the cover member including a grip portion which in use is acted upon by the user in the delivery of medicament and includes a surface having a component facing in the sense of rotation of the cover member from the open to the closed position; characterized in that the main body includes a projecting member which includes a surface having a component facing in the sense of rotation of the cover member from the closed to the open position behind which the surface of the grip portion of the cover member is at least partly located in the open position of the cover member, whereby in use in the delivery of medicament the surface of the grip portion of the cover member is caused to be urged behind the surface of the projecting member of the main body so as to lock the cover member relative to the main body.

Preferably, the projecting member of the main body includes a further surface having a component facing in the sense of rotation of the cover member form the open to the closed position for guiding the grip portion of the cover member over the projecting member of the main body on rotation of the cover member to the open position.

Preferably, the cover member includes first and second side members and at least one interconnecting member which interconnects the first and second side members.

More preferably, the grip portion of the cover member is provided by at least one interconnecting member.

Preferably, the grip portion of the cover member includes relief profiling.

More preferably, the relief profiling comprises a plurality of ribs.

Preferably, at least the grip portion of the cover member is sufficiently resilient as both to allow the surface of the grip portion of the cover member to be caused to be urged behind the surface of the projecting member of the main body in the open position of the cover member and to allow the grip portion of the cover member to be deformed to pass over the projecting member of the main body in freeing the cover member from the open position.

The present invention also extends to an inhaler comprising the above-described actuator and a canister containing medicament.

Preferably, the inhaler is a pressurised metered dose inhaler.

Preferably, in the open position of the cover member the grip portion of the cover member substantially opposes the axis of movement of the canister in use in the delivery of medicament.

A preferred embodiment of the present invention will now be described hereinbelow by way of example only with reference to the accompanying drawings, in which:

FIG. 3 illustrates a side view of the main body of the actuator of the inhaler of FIG. 1;

FIG. 4 illustrates a front view of the main body of FIG. 3;

FIG. 5 illustrates a rear view of the main body of FIG. 3;

FIG. 6 illustrates a plan view of the main body of FIG. 3;

FIG. 7 illustrates an underneath plan view of the main body of FIG. 3;

FIG. 8 illustrates a vertical sectional view (along section I—I in FIG. 6) of the main body of FIG. 3, illustrated with a canister fitted therein;

Figure 1:
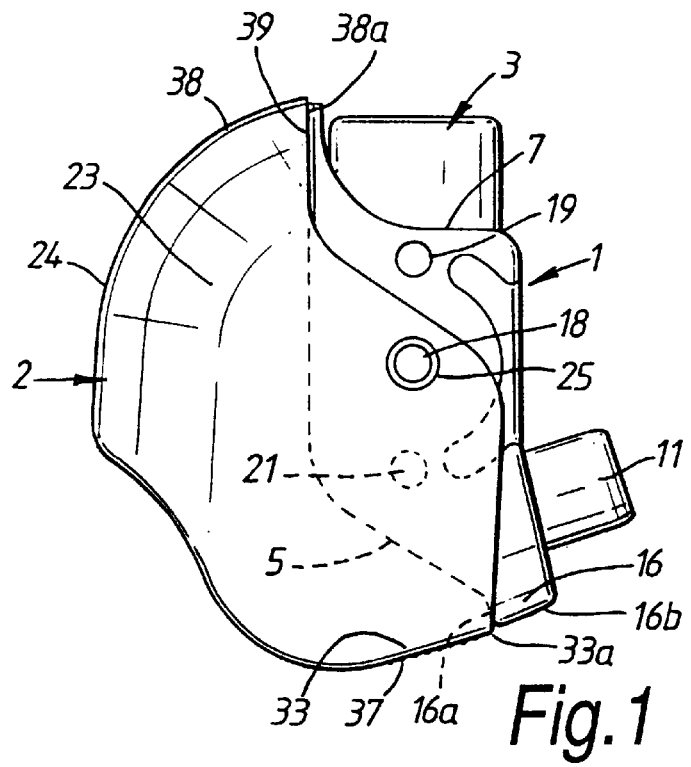
FIG. 1 illustrates a side view of an inhaler in accordance with a preferred embodiment of the present invention, with the cover member of the actuator in the open position.

The inhaler comprises an actuator, which comprises a main body 1 and a cover member 2 rotatably mounted thereto, and an aerosol canister 3 fitted therein.

The main body 1 defines a chamber 4 which has a substantially square cross-section, a closed lower end 5 and an open upper end 7 in which the canister 3 having a valve stem 10 extending therefrom is fitted. The main body 1 is preferably injection moulded from a plastics material such as polypropylene.

The main body 1 also includes an outlet 11, in this embodiment a tubular element of circular section, which is configured so as to be insertable into the nostril of a user. The outlet 11 is disposed at the lower end 5 of the main body 1 and extends upwardly from the front wall of the main body 1 so as to enclose an acute angle with the longitudinal axis thereof.

The main body 1 further includes a spray nozzle 13 disposed at the lower end 5 of the chamber 4. The spray nozzle 13 is adapted to receive the valve stem 10 of the canister 3 and is arranged to direct an aerosol spray through the outlet 11.

The main body 1 yet further includes a projecting lip 16 which is downwardly-directed from the lower end 5 of the main body 1. The projecting lip 16 includes a first surface 16a having a rearwardly-directed component which acts as a locking surface and a second surface 16b having a forwardly-directed component which acts as a guiding surface.

The main body 1 still further includes a projecting stud 18 and first and second blind recesses 19, 21 on each side wall thereof. In this embodiment the studs 18 are located at the mid-point along the longitudinal length of the side walls of the main body 1 and the recesses 19, 21 are located symmetrically vertically above and below the studs 18. The purpose of the studs 18 and the recesses 19, 21 will become apparent hereinbelow.

Figure 2:
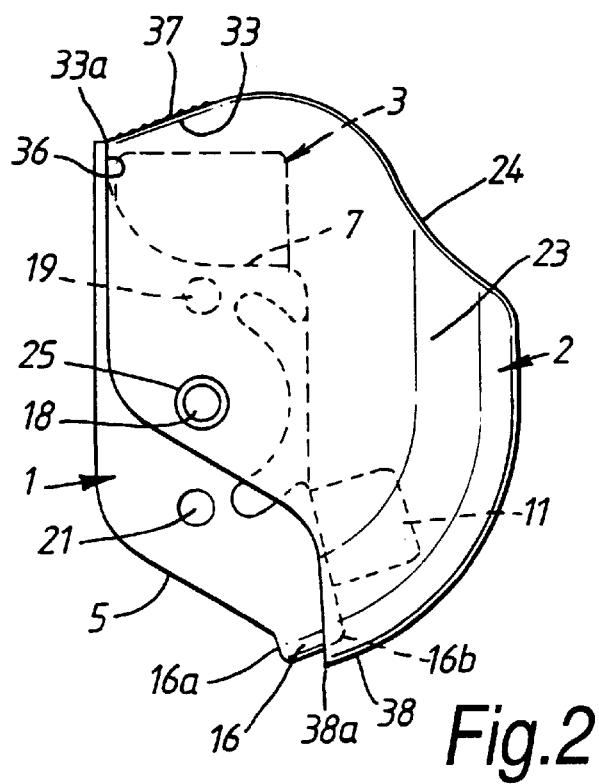
FIG. 2 illustrates a side view of the inhaler of FIG. 1, with the cover member of the actuator in the closed position.
Figure 9:
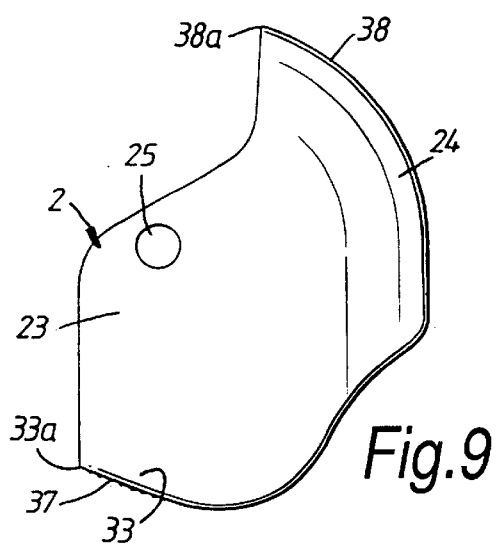
FIG. 9 illustrates a side view of the cover member of the actuator of the inhaler of FIG. 1.
Figure 11:
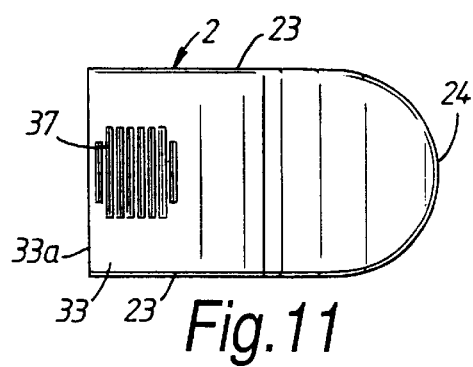
FIG. 11 illustrates an underneath plan view of the cover member of FIG. 9.
Figure 10:
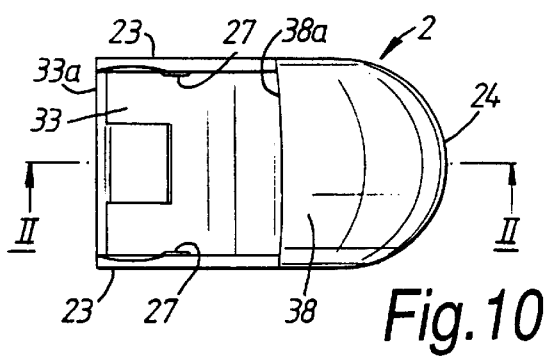
FIG. 10 illustrates a plan view of the cover member of FIG. 9.
Figure 12:
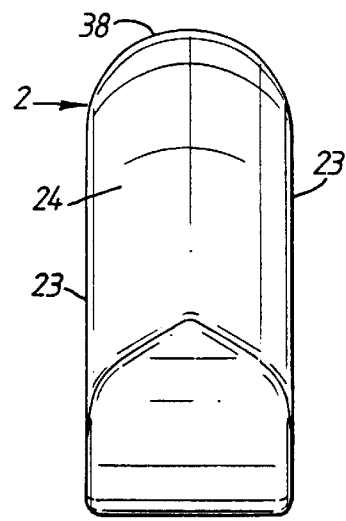
FIG. 12 illustrates a front view of the cover member of FIG. 9.
Figure 13:
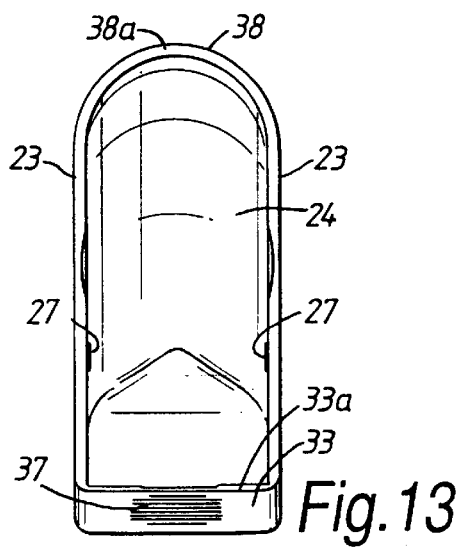
FIG. 13 illustrates a rear view of the cover member of FIG. 9.
Figure 14:
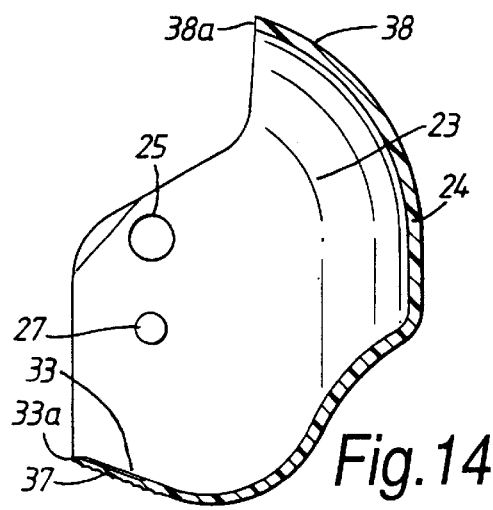
FIG. 14 illustrates a vertical sectional view (along section II—II in FIG. 10) of the cover member of FIG. 9.

The cover member 2 is rotatable relative to the main body 1 between a closed position (FIG. 2) in which the cover member 2 acts to enclose the canister 3 and the outlet 11 so as to protect the same and an open position (FIG. 1) in which the outlet 11 is exposed for use. The cover member 2 is preferably injection moulded from a transparent plastics material such as styrene acrylonitrile or polycarbonate. In using a transparent plastics material the indications on the canister 3 can be seen with the cover member 2 in the closed position.

The cover member 2 includes two substantially parallel side members 23 which are spaced to engage about the side walls of the main body 1, and an interconnecting member 24, in this embodiment arcuate in shape, which interconnects the side members 23.

The side members 23 of the cover member 2 each include an opposed opening 25, which openings 25 are arranged to locate on the respective projecting studs 18 on the side walls of the main body 1 and allow rotation of the cover member 2 in relation to the main body 1, and an inwardly projecting stud 27, which studs 27 are adapted to locate in the first and second recesses 19, 21 in the main body 1 in the closed and the open positions of the cover member 2 respectively.

The interconnecting member 24 includes a first, grip portion 33 which in the open position of the cover member 2 is acted upon by the user in the delivery of medicament and includes a surface 33a which acts as a locking surface as will be described hereinbelow. In the closed position of the cover member 2 the surface 33a of the grip portion 33 abuts a first part 36 of the main body 1, in this embodiment the front surface of the upper end of the rear wall of the main body 1, to define a limit of rotation of the cover member 2. The grip portion 33 also includes a plurality of ribs 37 for clearly identifying where the user should ideally place his/her thumb.

The interconnecting member 24 further includes a second portion 38 which includes a surface 38a which in the open position of the cover member 2 abuts a second part 39 of the main body 1, in this embodiment the rear surface of the upper end of the rear wall of the main body 1, to define a limit of rotation of the cover member 2.

Figure 15:
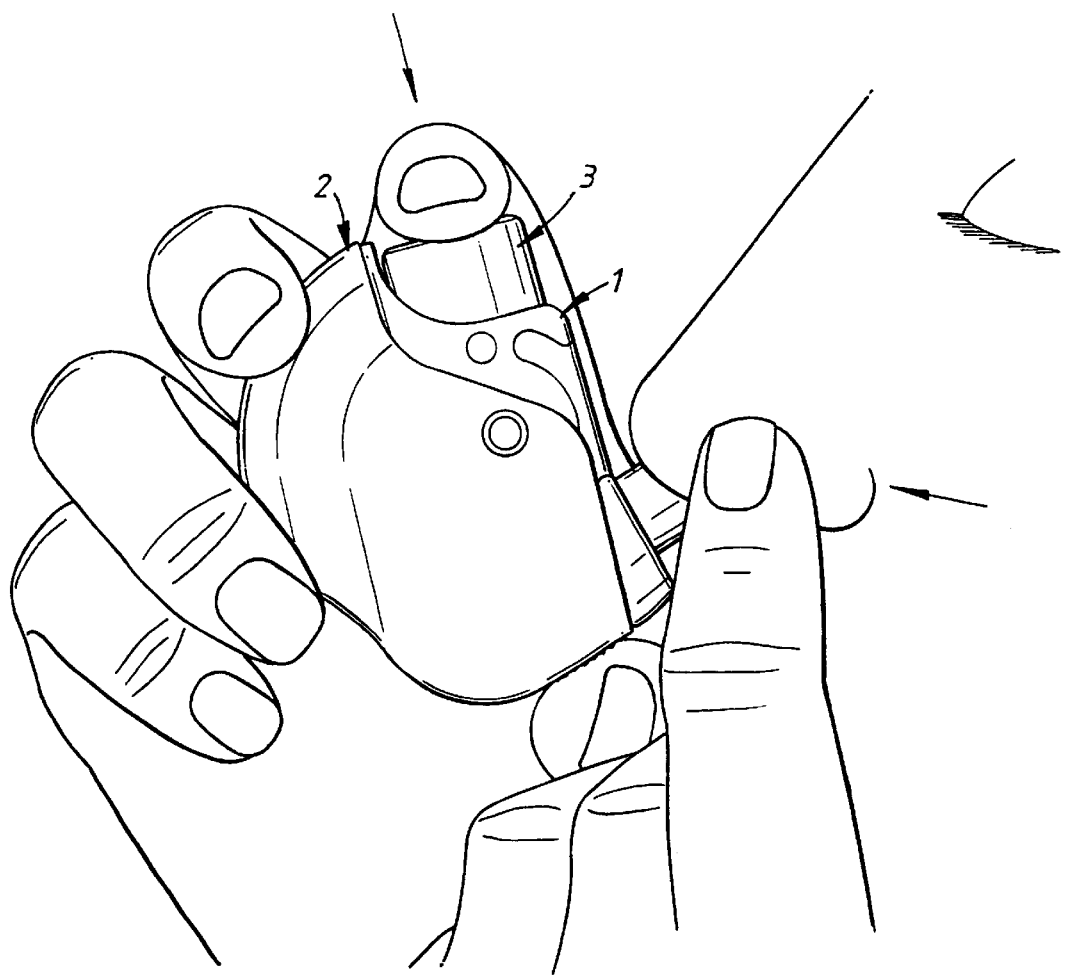
FIG. 15 illustrates the inhaler of FIG. 1 in use.

In use, from the closed position (FIG. 2), the user rotates the cover member 2 relative to the main body 1, in the illustrated orientation in the clockwise sense. At a position near the open position of the cover member 2, the surface 33a of the grip portion 33 of the cover member 2 contacts the guiding surface 16b of the projecting lip 16 of the main body 1. With continued rotation of the cover member 2 the surface 33a of the grip portion 33 of the cover member 2 rides up the guiding surface 16b of the projecting lip 16 of the main body 1 and becomes progressively more deformed. This deformation continues until the surface 33a of the grip portion 33 of the cover member 2 passes over the guiding surface 16b of the projecting lip 16 of the main body 1 and snaps back behind the locking surface 16a of the projecting lip 16 of the main body 1 so as to lock the cover member 2 in the open position. In this position the inhaler is ready for use. The user then takes the inhaler in his/her hand as illustrated in FIG. 15 and inserts the outlet 11 of the actuator into one of his/her nostrils, at the same time closing the other nostril. The user then holds his/her breath and actuates the canister 3 to administer a metered dose of medicament. After actuation of the canister 3, the user withdraws the outlet 11 of the actuator from his/her nostril and repeats the procedure for the other nostril. The user then returns the cover member 2 to the closed position. From the open position (FIG. 1), the user deforms the cover member 2 slightly to move the surface 33a of the grip portion 33 of the cover member 2 radially outwardly sufficiently to allow the cover member 2 to be rotated, in the illustrated orientation in the anti-clockwise sense, and returned to the closed position. In the closed position the cover member 2 is held in place by location of the inwardly projecting studs 27 on the side members 23 of the cover member 2 in the respective ones of the first recesses 19 in the side walls of the main body 1.

It will be appreciated that the configuration of the locking mechanism provided by the locking surface 16a of the projecting lip 16 of the main body 1 and the locking surface 33a of the grip portion 33 of the cover member 2 is particularly advantageous in that during actuation of the canister 3, when locking of the cover member 2 in the open position is actually most required, the locking action is most effective since the actuation force applied by the user actively causes the locking surface 33a of the grip portion 33 of the cover member 2 to be urged behind the locking surface 16a of the projecting lip 16 of the main body 1. Indeed, the locking mechanism is such that the greater the force applied by the user during the actuation of the canister 3, the greater the extent to which the locking surface 33a of the grip portion 33 of the cover member 2 is urged behind the locking surface 16a of the projecting lip 16 of the main body 1 and the more definite the locking action.

Finally, it will be understood that the present invention is not restricted to the described embodiment but can be modified in many different ways without departing from the scope of the appended claims.

What is claimed is:

1. An actuator for an inhaler for administering medicament by inhalation comprising: a main body defining a chamber for receiving a canister containing medicament, and including an outlet through which medicament is in use delivered, the canister being in use acted upon by the user in the delivery of medicament;

a cover member rotatable in relation to the main body between a first, closed position in which the outlet is covered and a second, open position in which the outlet is exposed, the cover member including a grip portion which in use is acted upon by the user in the delivery of medicament and includes a surface having a component facing in the direction of rotation of the cover member from the open to the closed position;

characterized in that the main body includes a projecting member which includes a surface having a component facing in the direction of rotation of the cover member from the closed to the open position behind which the surface of the grip portion of the cover member is at least partly located in the open position of the cover member, whereby in use in the delivery of medicament the surface of the grip portion of the cover member is caused to be urged behind the surface of the projecting member of the main body so as to lock the cover member relative to the main body.

2. The actuator according to claim 1, wherein the projecting member of the main body includes a further surface having a component facing in the direction of rotation of the cover member from the open to the closed position for guiding the grip portion of the cover member over the projecting member of the main body on rotation of the cover member to the open position.

3. The actuator according to claim 1, wherein the cover member includes first and second side members and an interconnecting member which interconnects the first and second side members.

4. The actuator according to claim 3, wherein the grip portion of the cover member is provided by said interconnecting member.

5. The actuator according to claim 1, wherein the grip portion of the cover member includes relief profiling.

6. The actuator according to claim 5, wherein the relief profiling comprises a plurality of ribs.

7. The actuator according to claim 1, wherein at least the grip portion of the cover member is sufficiently resilient as both to allow the surface of the grip portion of the cover member to be caused to be urged behind the surface of the projecting member of the main body in the open position of the cover member and to allow the grip portion of the cover member to be deformed to pass over the projecting member of the main body in freeing the cover member from the open position.

8. An inhaler comprising the actuator according to claim 1 and a canister containing medicament.

9. An inhaler according to claim 8, wherein the inhaler is a pressurized metered dose inhaler.

10. The inhaler according to claim 8, wherein in the open position of the cover member the grip portion of the cover member substantially opposes an axis of movement of the canister in use in the delivery of medicament.

* * * * *